(12) United States Patent
Triplett et al.

(10) Patent No.: US 7,686,809 B2
(45) Date of Patent: Mar. 30, 2010

(54) ROD INSERTER AND ROD WITH REDUCED DIAMETER END

(75) Inventors: Daniel Triplett, Logan, UT (US); T. Wade Fallin, Hyde Park, UT (US); Karen Mohr, Logan, UT (US); Thierry Millard, Cestas (FR)

(73) Assignee: Stryker Spine (FR)

( * ) Notice: Subject to any disclaimer, the term of this patent is extended or adjusted under 35 U.S.C. 154(b) by 484 days.

(21) Appl. No.: 11/651,442

(22) Filed: Jan. 9, 2007

(65) Prior Publication Data

US 2008/0077136 A1 Mar. 27, 2008

Related U.S. Application Data

(60) Provisional application No. 60/847,009, filed on Sep. 25, 2006.

(51) Int. Cl.
*A61F 5/00* (2006.01)
(52) U.S. Cl. ........................................ 606/86 A; 606/99
(58) Field of Classification Search ............... 606/86 A, 606/86 B, 86 R, 99, 104, 279, 914; 24/600.6, 24/601.7; 132/212, 270
See application file for complete search history.

(56) References Cited

U.S. PATENT DOCUMENTS

| 311,941 | A | * | 2/1885 | Armstrong | .................. | 24/600.6 |
| 486,419 | A | * | 11/1892 | Pearson et al. | ................. | 24/3.13 |

(Continued)

FOREIGN PATENT DOCUMENTS

DE 4238339 5/1994

(Continued)

OTHER PUBLICATIONS

Sofamor Danek; Eclipse CD Horizon Eclipse Implants and Instruments, Information from the Sofamor Danek Web page, p. 1-3.

(Continued)

*Primary Examiner*—Eduardo C Robert
*Assistant Examiner*—Devanie Dufour
(74) *Attorney, Agent, or Firm*—Lerner, David, Littenberg, Krumholz & Mentlik, LLP

(57) ABSTRACT

An inserter tool for coupling a spinal rod with an implant includes an outer shaft having a proximal end, a distal end and an elongated opening extending between the proximal and distal ends, a handle secured to the proximal end of the outer shaft, and an inner shaft having a proximal end and a distal end, the inner shaft being telescopically received within the elongated opening of the outer shaft and being adapted to move between the proximal and distal ends of the outer shaft. The tool includes a compressible clamping tip secured to the distal end of the inner shaft, the clamping tip including a first section secured to the distal end of the inner shaft, a flexible arm that extends from the first section, and an opening disposed between the first section and the flexible arm. A knob is coupled with the proximal end of the inner shaft, the knob being rotatable in a first direction for extending the clamping tip from the distal end of the outer shaft and in a second direction for retracting the clamping tip into the distal end of the outer shaft so as to compress the flexible arm of the clamping tip toward the first section of the clamping tip.

17 Claims, 8 Drawing Sheets

U.S. PATENT DOCUMENTS

| | | | |
|---|---|---|---|
| 649,515 A * | 5/1900 | Grozinger | 24/600.6 |
| 979,641 A * | 12/1910 | Brash | 24/600.6 |
| 1,200,540 A * | 10/1916 | Swedlund | 24/601.6 |
| 3,365,759 A * | 1/1968 | Molzan et al. | 24/600.6 |
| 3,877,434 A * | 4/1975 | Ferguson et al. | 606/158 |
| 4,086,926 A * | 5/1978 | Green et al. | 606/143 |
| 4,409,968 A | 10/1983 | Drummond | |
| 4,411,259 A | 10/1983 | Drummond | |
| 4,448,191 A | 5/1984 | Rodnyansky et al. | |
| 4,592,347 A * | 6/1986 | Mahruki | 606/206 |
| 4,877,020 A * | 10/1989 | Vich | 606/86 R |
| 4,927,425 A | 5/1990 | Lozier | |
| 4,955,885 A | 9/1990 | Meyers | |
| 5,129,388 A | 7/1992 | Vignaud et al. | |
| 5,192,288 A * | 3/1993 | Thompson et al. | 606/143 |
| 5,217,461 A | 6/1993 | Asher et al. | |
| 5,360,431 A | 11/1994 | Puno et al. | |
| 5,364,397 A * | 11/1994 | Hayes et al. | 606/86 A |
| 5,417,230 A * | 5/1995 | Wood | 132/212 |
| 5,472,439 A * | 12/1995 | Hurd | 606/1 |
| 5,476,464 A | 12/1995 | Metz-Stavenhagen et al. | |
| 5,480,440 A | 1/1996 | Kambin | |
| 5,499,997 A * | 3/1996 | Sharpe et al. | 606/206 |
| 5,591,165 A | 1/1997 | Jackson | |
| 5,616,143 A | 4/1997 | Schlapfer et al. | |
| 5,624,442 A | 4/1997 | Mellinger et al. | |
| 5,672,176 A | 9/1997 | Biedermann et al. | |
| 5,720,751 A | 2/1998 | Jackson | |
| 5,733,286 A | 3/1998 | Errico et al. | |
| 5,782,747 A * | 7/1998 | Zimmon | 600/104 |
| 5,782,830 A * | 7/1998 | Farris | 606/99 |
| 5,910,141 A | 6/1999 | Morrison et al. | |
| 5,928,232 A | 7/1999 | Howland et al. | |
| 5,938,662 A | 8/1999 | Rinner | |
| 5,993,474 A * | 11/1999 | Ouchi | 606/206 |
| 6,015,409 A | 1/2000 | Jackson | |
| 6,036,692 A | 3/2000 | Burel et al. | |
| 6,099,528 A | 8/2000 | Saurat et al. | |
| 6,102,912 A | 8/2000 | Cazin et al. | |
| 6,123,707 A | 9/2000 | Wagner | |
| 6,226,548 B1 | 5/2001 | Foley et al. | |
| 6,235,028 B1 | 5/2001 | Brumfield et al. | |
| 6,319,257 B1 * | 11/2001 | Carignan et al. | 606/99 |
| 6,530,929 B1 | 3/2003 | Justis et al. | |
| 6,726,692 B2 | 4/2004 | Bette | |
| 6,746,449 B2 | 6/2004 | Jones et al. | |
| 6,790,208 B2 | 9/2004 | Oribe et al. | |
| 6,821,277 B2 | 11/2004 | Teitelbaum | |
| 6,875,212 B2 | 4/2005 | Shaolian et al. | |
| 6,964,667 B2 | 11/2005 | Shaolian et al. | |
| 6,976,988 B2 * | 12/2005 | Ralph et al. | 606/99 |
| 7,008,422 B2 | 3/2006 | Foley et al. | |
| 7,008,424 B2 | 3/2006 | Teitelbaum | |
| 7,011,660 B2 | 3/2006 | Sherman et al. | |
| 7,083,621 B2 | 8/2006 | Shaolian et al. | |
| 7,169,182 B2 * | 1/2007 | Errico et al. | 623/17.15 |
| 7,188,626 B2 | 3/2007 | Foley et al. | |
| 2001/0000348 A1 * | 4/2001 | Chu et al. | 606/113 |
| 2001/0027318 A1 | 10/2001 | Oribe et al. | |
| 2002/0045904 A1 | 4/2002 | Fuss et al. | |
| 2002/0068975 A1 | 6/2002 | Teitelbaum et al. | |
| 2002/0082598 A1 | 6/2002 | Teitelbaum | |
| 2002/0082600 A1 | 6/2002 | Shaolian et al. | |
| 2002/0095153 A1 | 7/2002 | Jones et al. | |
| 2002/0188295 A1 * | 12/2002 | Martz et al. | 606/61 |
| 2002/0198526 A1 | 12/2002 | Shaolian et al. | |
| 2003/0009168 A1 * | 1/2003 | Beale et al. | 606/61 |
| 2003/0014057 A1 * | 1/2003 | Ralph et al. | 606/99 |
| 2003/0028195 A1 | 2/2003 | Bette | |
| 2003/0060824 A1 | 3/2003 | Viart et al. | |
| 2003/0073998 A1 | 4/2003 | Pagliuca et al. | |
| 2003/0083747 A1 * | 5/2003 | Winterbottom et al. | 623/17.11 |
| 2003/0208203 A1 | 11/2003 | Lim et al. | |
| 2003/0225408 A1 | 12/2003 | Nichols et al. | |
| 2004/0006341 A1 | 1/2004 | Shaolian et al. | |
| 2004/0006344 A1 | 1/2004 | Nguyen et al. | |
| 2004/0034351 A1 | 2/2004 | Sherman et al. | |
| 2004/0039384 A1 | 2/2004 | Boehm et al. | |
| 2004/0068269 A1 * | 4/2004 | Bonati et al. | 606/104 |
| 2004/0082954 A1 | 4/2004 | Teitelbaum et al. | |
| 2004/0082961 A1 | 4/2004 | Teitelbaum | |
| 2004/0087950 A1 | 5/2004 | Teitelbaum | |
| 2004/0102790 A1 * | 5/2004 | Ralph et al. | 606/99 |
| 2004/0172022 A1 | 9/2004 | Landry et al. | |
| 2005/0038445 A1 * | 2/2005 | Errico et al. | 606/99 |
| 2005/0090824 A1 * | 4/2005 | Shluzas et al. | 606/61 |
| 2005/0171538 A1 * | 8/2005 | Sgier et al. | 606/61 |
| 2005/0171540 A1 | 8/2005 | Lim et al. | |
| 2005/0228392 A1 * | 10/2005 | Keyer et al. | 606/86 |
| 2005/0273171 A1 | 12/2005 | Gordon et al. | |
| 2006/0030839 A1 | 2/2006 | Park et al. | |
| 2006/0111714 A1 | 5/2006 | Foley | |
| 2006/0200135 A1 | 9/2006 | Sherman et al. | |
| 2006/0235426 A1 * | 10/2006 | Lim et al. | 606/99 |
| 2008/0009880 A1 * | 1/2008 | Warnick et al. | 606/99 |
| 2008/0039860 A1 * | 2/2008 | Trudeau | 606/99 |

FOREIGN PATENT DOCUMENTS

| | | |
|---|---|---|
| DE | 10027988 | 1/2002 |
| EP | 1006888 | 6/2000 |
| EP | 1 138 265 | 10/2001 |
| EP | 1374786 | 1/2004 |
| EP | 1545355 | 6/2005 |
| SU | 839513 | 6/1981 |
| WO | 9514437 | 6/1995 |
| WO | 96/15729 | 5/1996 |
| WO | 97/32533 | 9/1997 |
| WO | 03020110 | 3/2003 |
| WO | WO 03/020110 | 3/2003 |
| WO | 03028566 | 4/2003 |
| WO | WO 03/028566 | 4/2003 |
| WO | 04004584 | 1/2004 |
| WO | WO 2004/004854 | 1/2004 |
| WO | 2004/021899 | 3/2004 |
| WO | 04017847 | 3/2004 |
| WO | 04021899 | 3/2004 |
| WO | WO 2004/017847 | 3/2004 |
| WO | 2004/037074 | 5/2004 |
| WO | 2004/041100 | 5/2004 |
| WO | 04037074 | 5/2004 |
| WO | 04041100 | 5/2004 |
| WO | 2004/058045 | 7/2004 |
| WO | 04058045 | 7/2004 |
| WO | 05018466 | 3/2005 |
| WO | 05023123 | 3/2005 |
| WO | 2005018466 | 3/2005 |
| WO | 2005023123 | 3/2005 |
| WO | 05032358 | 4/2005 |
| WO | 2005032358 | 4/2005 |
| WO | 2005060534 | 7/2005 |
| WO | 2005/072081 | 8/2005 |
| WO | 05072081 | 8/2005 |
| WO | 06116662 | 11/2006 |
| WO | WO2006/116662 | 11/2006 |

OTHER PUBLICATIONS

Charles Hartjen; The Atavi System, Surgical Technique Brochure. Endius, p. 1-I7.

Diapason, Surgical Texchnique Catalog, Diapasan Spinal System, Jan. 2002.

Pathfinder; Minimally Invasive Pedicle Fixation System. Spinal Concepts Product Brochure p. 1-4.

Pathfinder; Minimally invasive Spinal Fixation System and Surgical Technique. Spinal Concepts Product Brochure, p. 1-26.

Sofamor Danek; Eclipse CD Horizon Eclipse Implants and Instruments, Information from the Sofamor Danek Web page, p. 1-3, 2005.

Sofamor Danek; Sextant CD Horizon Sextant Rod Insertion System, Sofamor Danek Web page.

Sofamor Danek; Sextant CD Horizon Sextant Rod Insertion System. Surgical Techniqu Techniques p. 1-29.

* cited by examiner

ROD INSERTER AND ROD WITH REDUCED DIAMETER END

CROSS-REFERENCE TO RELATED APPLICATIONS

The present application claims the benefit of U.S. Provisional Application Ser. No. 60/847,009, filed Sep. 25, 2006, the disclosure of which is hereby incorporated by reference herein. The present application is related to U.S. patent application Ser. No. 11/526,785, entitled, "Rod Contouring Apparatus and Method for Percutaneous Pedicle Screw Extension," filed Sep. 25, 2006, which claims the benefit of U.S. Provisional Application No. 60/765,606, filed Feb. 6, 2006, the disclosures of which are hereby incorporated by reference herein.

BACKGROUND OF THE INVENTION

The present invention generally relates to spinal stabilization systems and more specifically relates to pedicle screw assemblies and tooling used with pedicle screw assemblies.

The spinal column is a highly complex system of bones and connective tissues that provides support for the body and protects the delicate spinal column and nerves. The spinal column includes a series of vertebrae stacked one atop the other, whereby each vertebral body includes a relatively strong bone portion forming the outside surface of the body (cortical) and a relatively weak bone portion forming the center of the body (cancellous). Situated between each vertebral body is an intervertebral disc that provides for cushioning and dampening of compressive forces applied to the spinal column. The vertebral canal containing the delicate spinal cords and nerves is located just posterior to the vertebral bodies.

Various types of spinal column disorders are known and include scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease or trauma, such as ruptured or slipped discs, degenerative disc disease, fractured vertebra, and the like. Patients that suffer from such conditions usually experience extreme and debilitating pain as well as diminished nerve function.

In order to correct or alleviate the above-mentioned disorders, spinal fixation procedures have been developed whereby surgical implants are used for fusing together and/or mechanically immobilizing adjacent vertebrae of the spine. Spinal fixation may also be used to alter the alignment of the adjacent vertebrae relative to one another so as to alter the overall alignment of the spine. Such techniques have been used effectively to treat the above-described conditions and, in most cases, to relieve pain suffered by the patient. However, as will be set forth in more detail below, there are some disadvantages associated with current fixation devices.

One particular spinal fixation procedure includes immobilizing the spine by using orthopedic rods, commonly referred to as spine rods or spinal stabilizing rods, that run generally parallel to the spine. This is accomplished by exposing the spine posteriorly and fastening bone screws to the pedicles of the appropriate vertebrae. The pedicle screws are generally placed two per vertebra, one at each pedicle on either side of the spinous process, and serve as anchor points for the spine rods. Clamping elements adapted for receiving a spine rod therethrough are then used to join the spine rods to the screws. The aligning influence of the rods forces the spine to conform to a more desirable shape. In certain instances, the spine rods may be bent to achieve the desired curvature of the spinal column.

U.S. Pat. No. 5,129,388 to Vignaud et al. discloses a spinal fixation device including a pedicle screw having a U-shaped head rigidly connected to the screw. The U-shaped head includes a U-shaped channel for receiving a spine rod therein. The U-shaped head is internally threaded so that a set screw having external threads may be screwed therein. After the pedicle screw has been inserted into bone and the spine rod is positioned in the U-shaped channel, the set screw is threaded into the internal threads of the coupling element for securing the spine rod in the U-shaped channel and blocking relative movement between the spine rod and the pedicle screw. The fixation device also includes a cap covering an upper portion of the U-shaped element to prevent the arms of the U-shaped element from spreading upon threading the set screw into the U-shaped head.

Surgeons have frequently encountered considerable difficulty when attempting to insert spinal fixation devices such as those disclosed in the above-mentioned '388 patent. For example, surgeons have frequently been unable to efficiently and adequately place the spine rod into the U-shaped heads of the bone screws. This is because the U-shaped heads of the screws are often not aligned with one another due to curvature in spines and the different orientations of the pedicles being instrumented. The spine rods are often bent in multiple planes in order to couple the pedicle screws to the rod, which may lead to weaker connections with the rod. These problems also result in significantly longer operations, thereby increasing the likelihood of complications associated with surgery.

In response to the problems noted in the '388 patent, U.S. Pat. No. 5,733,286 to Errico et al., U.S. Pat. No. 5,672,176 to Biedermann et al., and U.S. Pat. No. 5,476,464 to Metz-Stavenhagen disclose polyaxial spinal fixation devices wherein the anchoring element fixed to the bone has a spherically-shaped head. The fixation devices in the subject patents also have orthopedic rod capturing assemblies for securing orthopedic rods in the capturing assemblies and connecting the rods with the anchoring elements. The spherically shaped heads of the anchoring elements permit movement of the anchoring elements relative to the orthopedic rod capturing assemblies.

In spite of the above-mentioned devices, there remains a need for improved tools and techniques for inserting spine rods into the rod-capturing portions of pedicle screw assemblies. The also remains a need for improved spine rods that may be easily coupled with a pedicle screw assembly.

SUMMARY OF THE INVENTION

In certain preferred embodiments of the present invention, a rod insertion tool is disclosed that may be used for percutaneous insertion of a spinal rod. The rod insertion tool preferably holds the spinal rod firmly, but allows a user to clamp the spinal rod to the instrument in a plurality of different rod trajectories. By holding the spinal rod at the end, the rod may be inserted through a single point incision from a posterior approach down to the spinal implant (pedicle screw) heads. While still maintaining control of the rod using the inserter tool, the set screws for coupling the rod to the head of the pedicle screws may be tightened without letting go and losing control of the spinal rod. Once the spinal rod is secured in the spinal implant, the insertion tool may be loosened to disengage the tool from the rod and to remove the insertion tool from the surgical site.

In certain preferred embodiments of the present invention, an inserter tool for coupling a spinal rod with an implant includes an outer shaft having a proximal end, a distal end and an elongated opening extending between the proximal and distal ends, and a handle secured to the proximal end of the outer shaft. The inserter tool desirably includes an inner shaft having a proximal end and a distal end, the inner shaft being telescopically received within the elongated opening of the outer shaft and being adapted to move between the proximal and distal ends of the outer shaft, and a compressible clamping tip secured to the distal end of the inner shaft, the clamping tip including a first section secured to the distal end of the inner shaft, a flexible arm that extends from the first section, and an opening disposed between the first section and the flexible arm. A knob is desirably coupled with the proximal end of the inner shaft, the knob being rotatable in a first direction for extending the clamping tip from the distal end of the outer shaft and in a second direction for retracting the clamping tip into the distal end of the outer shaft so as to compress the flexible arm of the clamping tip toward the first section of the clamping tip.

The tool may also include a socket disposed in the opening of the clamping tip, the socket having a slot that enables the socket to be compressed. The socket may be a ball socket having an aperture adapted to receive a stabilizing rod. The opening of the clamping tip defines an inner surface and the ball socket has an outer surface with a plurality of notches formed therein that are adapted to engage the inner surface of the opening.

In certain preferred embodiments of the present invention, the inner shaft extends through the handle for being attached to the knob. The proximal end of the inner shaft desirably has threads and the knob has a female opening with internal threads that are adapted to receive the threads of the inner shaft.

In certain preferred embodiments, the clamping tip has a hook shape and the flexible arm of the clamping tip has a shoulder that is engageable with the distal end of the outer shaft when the inner shaft is retracted relative to the outer shaft. The flexible arm of the clamping tip is preferably connected with the first section of the clamping tip through a flexible intermediate section. The flexible intermediate section desirably has a curved surface that extends between the first section of the clamping tip and the flexible arm of the clamping tip.

A stabilizing rod is desirably secured by the clamping tip. In preferred embodiments, the stabilizing rod has at least one end with a reduced diameter and the clamping tip is engageable with the reduced diameter end. The reduced diameter end may have a spherical surface.

In another preferred embodiment of the present invention, an inserter tool includes an outer shaft having a proximal end, a distal end and an elongated opening extending between the proximal and distal ends, a handle secured to the proximal end of the outer shaft, and an inner shaft telescopically received within the elongated opening of the outer shaft and being adapted to move between proximal and distal ends of the outer shaft the tool desirably includes a clamping tip secured to a distal end of the inner shaft, the clamping tip including a first section secured to the distal end of the inner shaft, a flexible arm that extends from the first section, and an opening disposed between the first section of the clamping tip and the flexible arm of the clamping tip. A knob is preferably coupled with a proximal end of the inner shaft, the knob being rotatable in a first direction for extending the clamping tip from the distal end of the outer shaft and in a second direction for retracting the clamping tip into the elongated opening at the distal end of the outer shaft so as to compress the flexible arm of the clamping tip toward the first section of the clamping tip.

A stabilizing rod may be secured by the clamping tip. The stabilizing rod may have first and second ends with at least one of the first and second ends having a reduced diameter relative to a remainder of the stabilizing rod. The reduced diameter end of the stabilizing rod may have a spherical surface.

In another preferred embodiment of the present invention, a pedicle screw assembly includes a bone fastener having a lower end for engaging bone and an upper end remote from the lower end, a head having a rod-receiving channel attached to the upper end of the bone fastener, and a spinal rod insertable into the rod-receiving channel of the head, the spinal rod having an outer surface extending between first and second ends thereof, whereby at least one of the first and second ends has a reduced diameter section.

In certain preferred embodiments, both of the first and second ends of the spinal rod have reduced diameter sections. The outer surface of the spinal rod preferably has a first diameter and the reduced diameter first and second ends of the spinal rod have second diameters that are smaller than the first diameter. In certain preferred embodiments, at least one of the first and second ends of the spinal rod has a spherical surface. In other preferred embodiments, both ends of the spinal rod have a spherical surface.

The spinal rod may be curved between the first and second ends thereof and the outer surface of the spinal rod has at least one alignment marker for identifying an axis of curvature of the spinal rod. The at least one alignment marker is desirably a line that extends along the axis of curvature of the spinal rod.

In another preferred embodiment of the present invention, a spinal rod has an outer surface extending between a first end and a second end thereof, wherein the outer surface of the spinal rod has a reduced diameter section at least one of the first and second ends. The one or more reduced diameter ends may have a spherical surface. The spinal rod may be curved between the first and second ends thereof, and the outer surface of the spinal rod has at least one alignment marker for identifying an axis of curvature of the spinal rod. The reduced diameter sections desirably have spherical surfaces and the outer surface of the spinal rod extending between the reduced diameter sections may have a cylindrical surface.

In certain preferred embodiments of the present invention, a spinal rod insertion tool includes an elongated outer shaft having a proximal end and a distal end, a handle secured to the proximal end of the outer shaft and a rotatable knob located at a proximal end of the knob. The outer shaft is preferably hollow and has an elongated opening that extends from the proximal end to the distal end thereof. The insertion tool also preferably has an inner shaft that is telescopically received with the outer shaft. The inner shaft has a proximal end that is coupled with the rotatable knob and a distal end that is located in the vicinity of the distal end of the outer shaft. As the knob is rotated, the inner shaft may be extended and retracted relative to the distal end of the outer shaft. The insertion tool also preferably include a collapsible clamping tip that is secured to the distal end of the inner shaft. The clamping tip has a central opening and a collapsible ring or ball may be positioned in the central opening. The clamping tip preferably has a free, flexible arm that may be elastically deformed toward a first section of the clamp tip when the clamp tip is retracted into the opening at the distal end of the outer shaft.

When the knob is rotated in a first direction, the inner shaft slides axially relative to the outer shaft and moves toward the proximal end of the tool. As the inner shaft moves toward the proximal end, the clamp tip in collapsed by its engagement with the opening at the distal end of the outer shaft, which in turn collapses the ball socket. If a spine rod is inserted into the ball socket and the ball socket collapsed, the ball socket will clamp down upon an outer surface of a spine rod.

In certain preferred embodiments, an inserter tool includes a handle having a first end coupled with a rotatable knob and a second end adapted to receive an outer shaft, the outer shaft having a central bore through which extends an inner shaft. The handle preferably has an outer surface, such as a knurled surface, that enables a user to hold onto the inserter tool. The outer shaft preferably has a first end adapted to connect to the handle, a second end adapted to receive a collapsible clamp tip and a central bore extending through the outer shaft that is designed to receive the inner shaft. The knob is rotatably attached to the handle and has a central threaded bore that engages with the inner shaft. In certain preferred embodiments, the inner shaft has a first threaded end that engages the knob and a second end adapted to connect to the collapsible clamp tip. By rotating or turning the knob, a user can selectively advance or retract the inner shaft relative to the outer shaft to clamp onto or release a spinal rod.

In certain preferred embodiments, the collapsible clamping tip has a first end adapted to connect to a distal end of the inner shaft, an opening adapted to receive a collapsible spherical ball, and a flexible arm that is compressible toward the first end of the clamping tip for compressing the collapsible spherical ball. The opening in the clamping tip enables the flexible arm to flex and collapse when the clamping tip is drawn into the outer shaft. The collapsible spherical ball has partial spherical geometry with a central bore that receives an end of a generally cylindrical spinal rod. The central bore is cut through to the surface of the collapsible spherical ball to allow the part to flex and collapse when acted upon by the collapsible clamp tip. The outer spherical surface of the collapsible spherical ball preferably has a plurality of small slots formed therein that provide edges for a higher friction bearing surface with the opening in the collapsible clamp tip. When the clamp tip is in an uncompressed state, the collapsible spherical ball is disposed within the spherical void of the collapsible clamp tip and is free to rotate relative to the clamp tip. When the clamp tip is in a compressed or clamped state, however, the collapsible spherical ball is prevented from rotating relative to the clamp tip due to the interaction between the high friction bearing surface on the outside of the collapsible spherical ball and the opening extending through the clamp tip.

In order to couple a stabilizing rod with one or more pedicle screws, a user may dispose a rod within the bore of a collapsible spherical ball and rotate the knob attached to the handle in a tightening or clockwise direction. Tightening the knob causes retraction of the inner shaft relative to the outer shaft so as to bring the collapsible clamp tip into contact with the distal end of the outer shaft. As the collapsible clamp tip is drawn into the opening at the distal end of the outer shaft, the flexible arm of the clamp tip is elastically compressed toward a first section of the clamp tip, which is turn causes the spherical ball to collapse onto the spinal rod. The collapsible spherical ball is held from rotation via the clamping action and the interaction of the high friction bearing surface of the ball with the collapsible clamp tip so as to hold the spinal rod firmly in position. Once the user has coupled the spinal rod with the pedicle screw implants, the rotatable knob is loosened for releasing the rod from the inserter tool. In operation, loosening the knob advances the inner shaft toward the distal end of the outer shaft, and extends the collapsible clamp tip from the outer shaft. Since the collapsible clamp tip and the collapsible spherical ball were previously only elastically deformed and not plastically deformed, the collapsible clamp tip and the collapsible spherical ball will uncompress or spring open to release the hold on the spinal rod, allowing the inserter instrument to disengage and be removed from the surgical site.

In other preferred embodiments of the present invention, the rotatable knob may include or be replaced by various other force input mechanisms such as levers, triggers, compound linkages, etc.

In still further preferred embodiments of the present invention, the clamping action may be provided by a movable external actuation shaft that is connected to the clamp tip at one end causing an opening and closing action of the clamp tip as the actuator bar is advanced or retracted and/or a movable internal actuation shaft with a tapered tip that engages with a tapered end of the split clamp to cause the opening and closing action of the clamp tip as the actuator bar is advanced or retracted.

Although the present invention is not limited by any particular theory of operation, it is believed that providing an inserter toll for a spinal rod as disclosed herein enables polyaxial adjustability of the orientation of the spinal rod within the rod inserter tool to accommodate various spinal rod insertion trajectories or approaches, while providing for a firm hold on the spinal rod during insertion. Moreover, the inserter tool disclosed herein facilitates percutaneous spinal rod insertion for minimal trauma and faster recovery for the patient.

These and other preferred embodiments of the present invention will be described in more detail below.

DETAILED DESCRIPTION

Figure 1A:
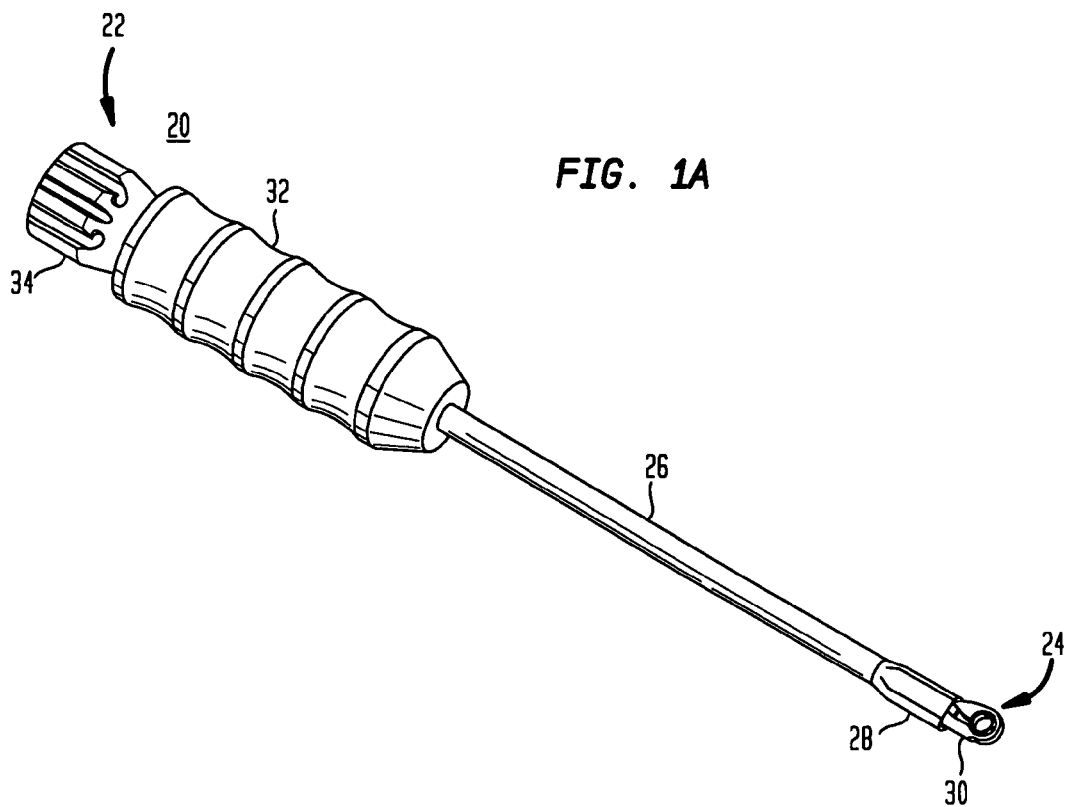
FIGS. 1A-1D show a rod inserter tool, in accordance with certain preferred embodiments of the present invention.
Figure 1B:
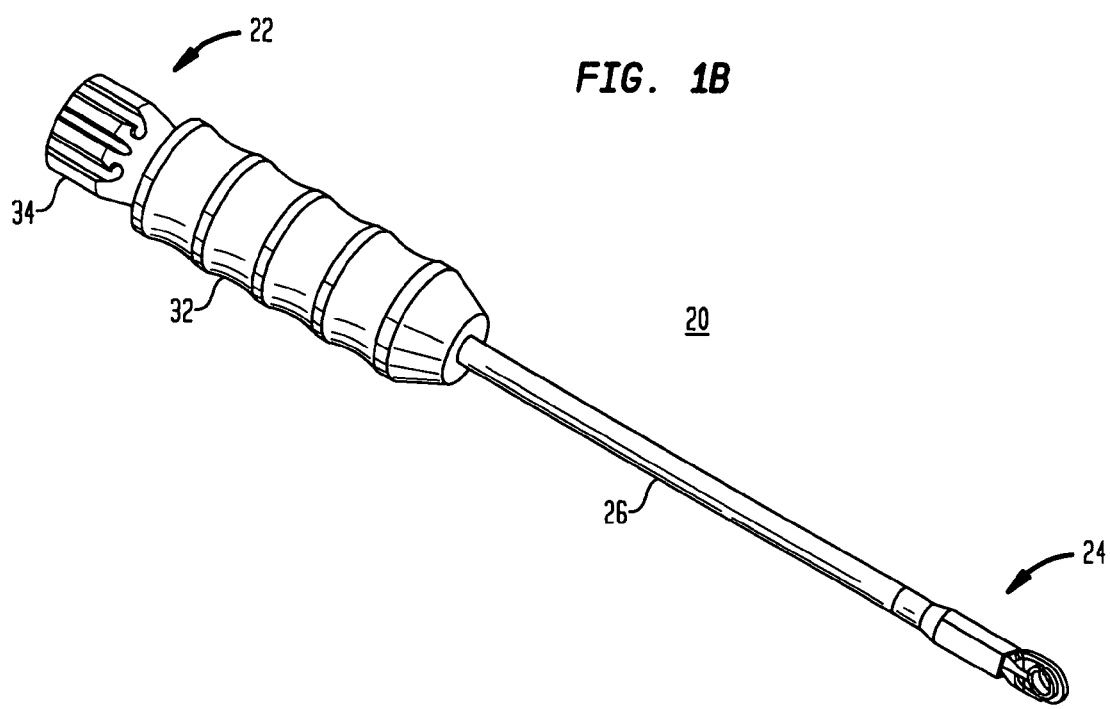

Referring to FIGS. 1A-1D, in certain preferred embodiments of the present invention, a rod inserter 20 has a proximal end 22 and a distal end 24 remote therefrom. The rod inserter 20 includes an outer shaft 26 having an elongated or longitudinally extending opening that extends from a proximal end 27 to a distal end 28 thereof. The rod inserter 20 also includes an inner shaft 30 (FIG. 1D) that is telescopically received within the outer shaft 26. The rod inserter 20 includes a handle 32 secured to the proximal end 27 of the outer shaft 26. The handle 32 is preferably secured to the outer shaft 26 so that the outer shaft is incapable of moving axially or rotationally relative to the handle 32. The rod inserter 20 also preferably includes a rotatable knob 34 that is rotated in a first direction for moving the inner shaft 30 axially toward the proximal end of the inserter tool and relative to the outer shaft 26, and in a second direction for retracting the inner shaft 30 into the outer shaft 26 and toward the proximal end 22 of the rod inserter 20.

Figure 1C:
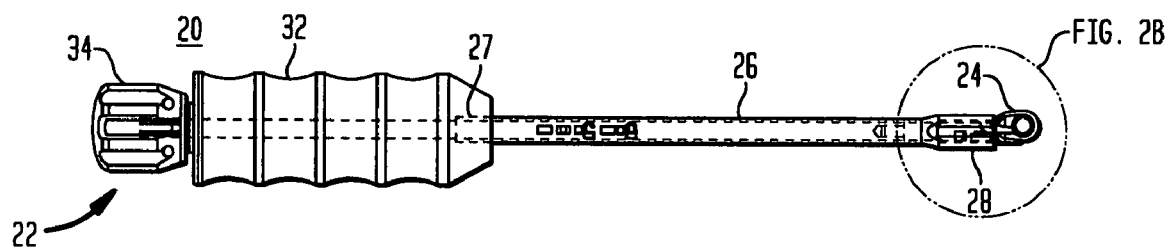
Figure 1D:
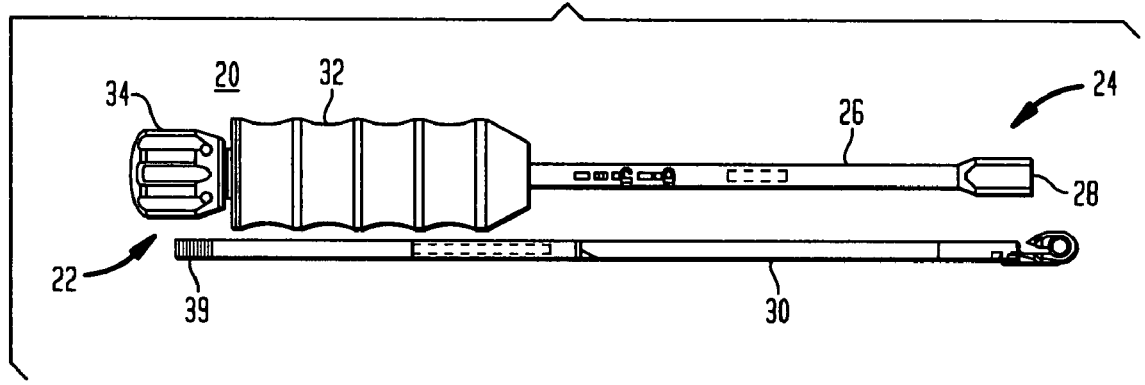
Figure 2A:
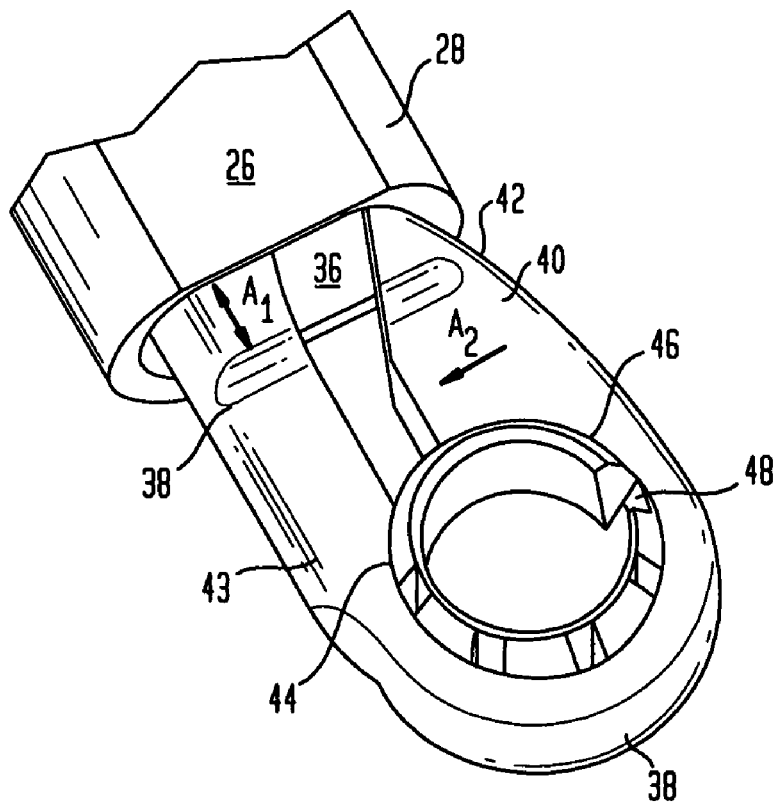
FIGS. 2A-2B show a distal end of the rod insertion tool shown in FIG. 1.
Figure 2B:
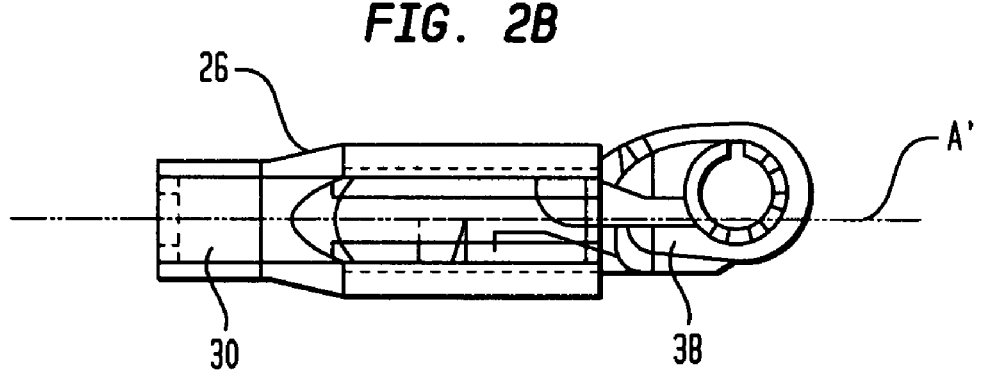

Referring to FIGS. 2A and 2B, the distal end 28 of the outer shaft 26 has an opening 36. As noted above, the opening 36 is preferably an elongated opening that extends toward the proximal end 27 of the outer shaft 26. A collapsible clamp tip 38 is preferably secured to a distal end of the inner shaft 30 and preferably projects from the opening 36 at the distal end 28 of the outer shaft 26. The inner shaft 30 preferably includes a proximal end 39 that is preferably coupled with the rotatable knob 34, as shown in FIG. 1C, and a distal end that is coupled with the collapsible clamp tip 38. As the rotatably knob 34 is rotated, the inner shaft 30 and the collapsible clamp tip 38 preferably move along the axis $A_1$ shown in FIGS. 2A and 2B.

Figure 3:
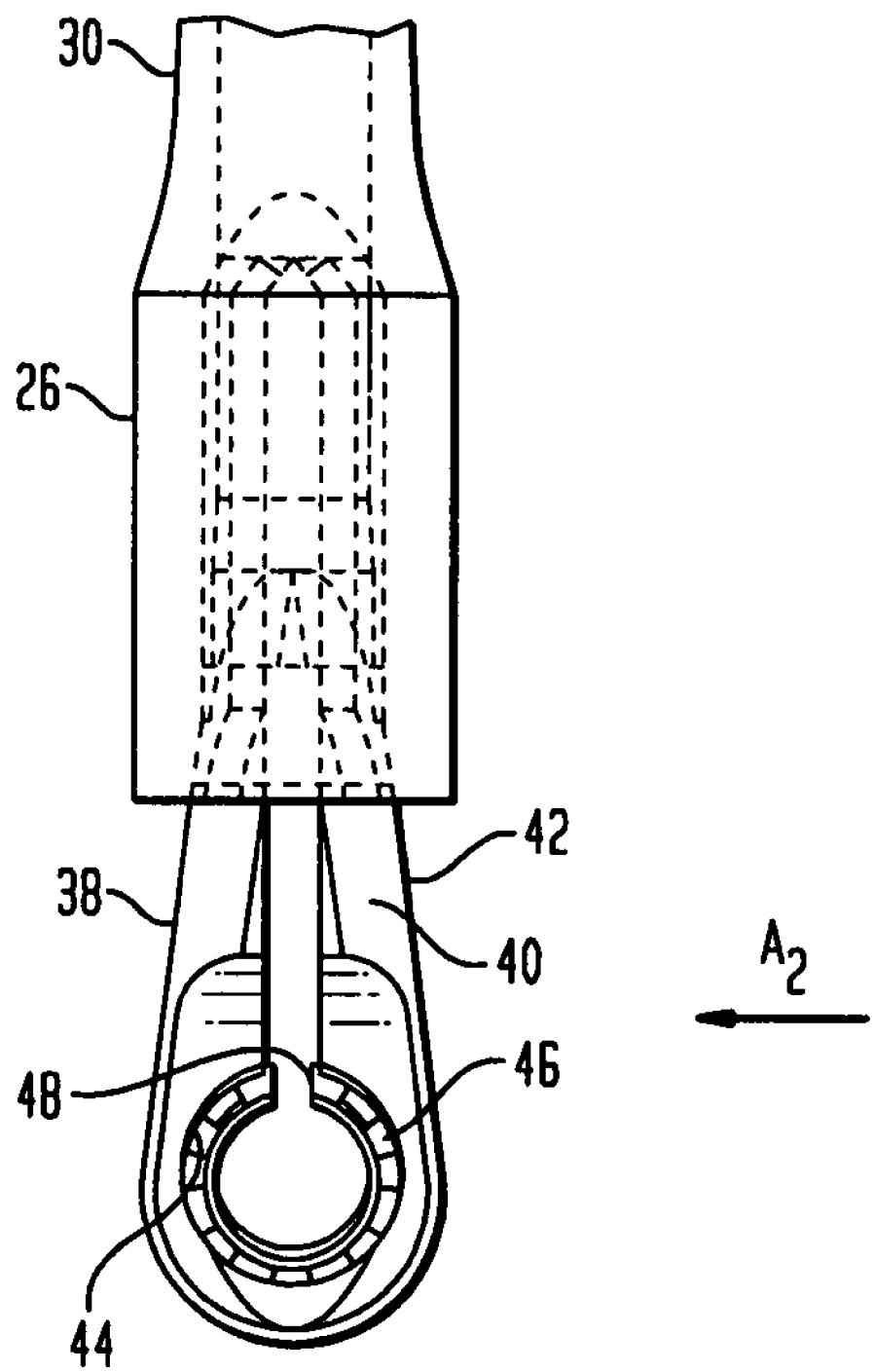
FIG. 3 shows another view of the distal end of the rod insertion tool shown in FIGS. 2A-2B.
Figure 4A:
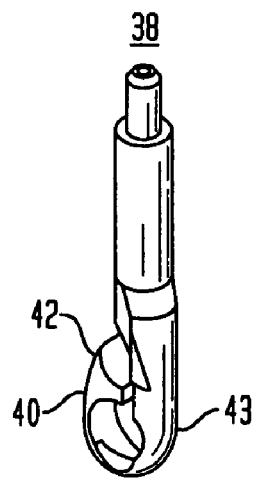
FIGS. 4A and 4B show a collapsible clamp tip for the rod inserter tool shown in FIGS. 1A-1D, in accordance with certain preferred embodiments of the present invention.
Figure 4B:
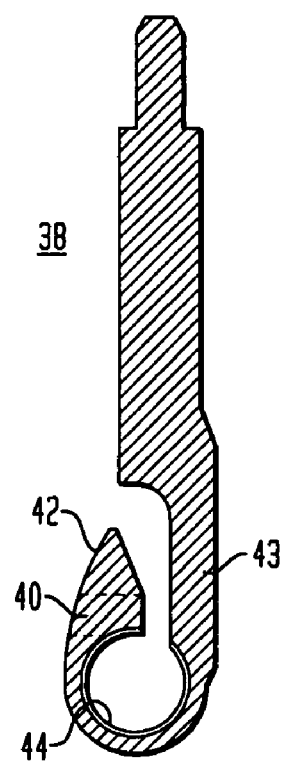
Figure 5A:
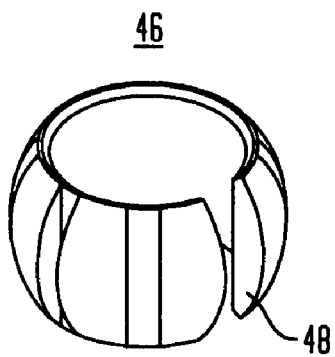
FIGS. 5A and 5B show a collapsible ball socket for the rod inserter tool shown in FIGS. 1A-1D, in accordance with certain preferred embodiments of the present invention.
Figure 5B:
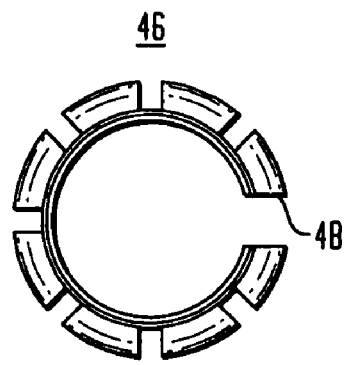

Referring to FIGS. 2A and 3, the collapsible clamp tip 38 also preferably includes a flexible arm 40 that desirably has a hook-like shape. The flexible arm 40 includes a shoulder 42 that is adapted to engage an inner surface of the outer shaft 26. In operation, as the inner shaft 30 is retracted toward the proximal end of the outer shaft 26, the shoulder 42 engages the inner surface of the outer shaft 26 for moving the flexible arm 40 toward a first section 43 of the clamp tip 38, in the direction indicated by the axis $A_2$.

Referring to FIGS. 2A and 3, the collapsible clamp tip 38 includes an opening 44 that is adapted to receive a collapsible ball socket 46 having a slot 48 that enables the collapsible ball socket 46 to be collapsed or compressed.

In certain preferred embodiments of the present invention, the inner shaft 30 is normally urged to project from the distal end 28 of outer shaft 26. The rod inserter 20 may include a spring-like element [not shown] that normally urges the outer shaft 30 into the extended position shown in FIGS. 2A-2B and 3. When it is desired to secure a spinal stabilizing rod using the insertion tool, an end of the rod is passed through the opening in the ball socket 46. The rotatable knob 34 is rotated for retracting the inner shaft 30 and the collapsible clamp tip 38 toward the proximal end 22 of the rod inserter. As the clamp tip 38 is pulled toward the proximal end of the rod inserter, the flexible arm 40 is compressed toward the first section 43 of the clamp tip 38, along the axis $A_2$ as shown in FIGS. 2A and 3. As the flexible arm 40 is compressed toward the first section 43, the collapsible ball socket 46 in the opening 44 of the clamp tip 38 is compressed, which in turn tightens the ball socket 46 about an outer surface of a stabilizing rod.

Figure 6:
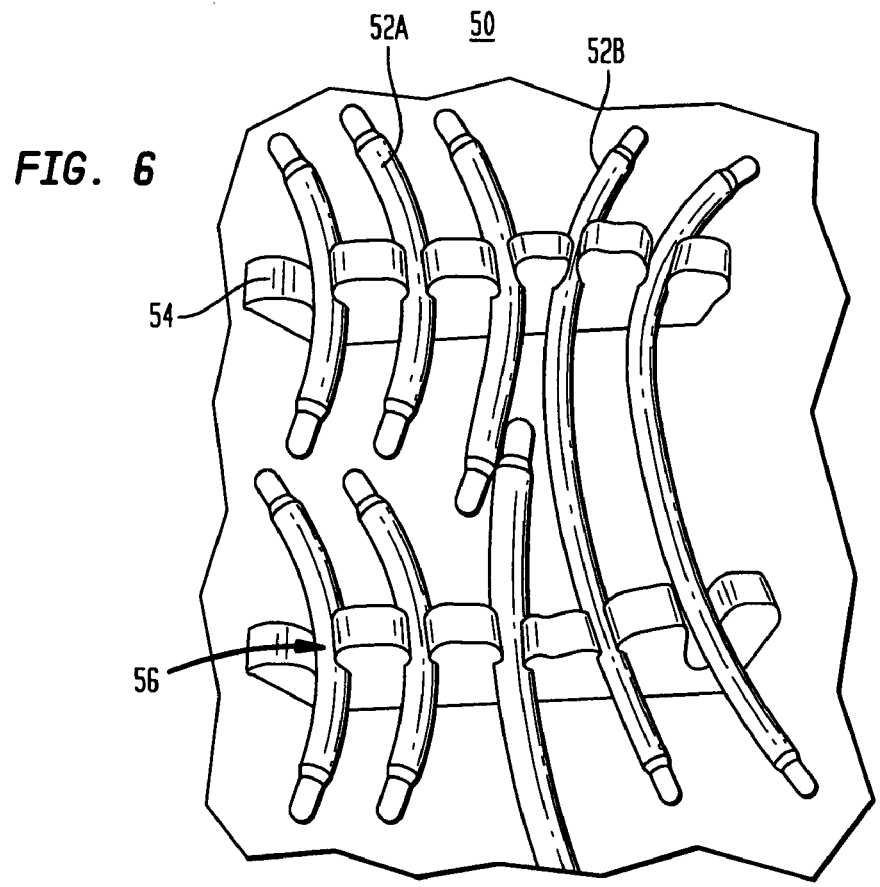
FIG. 6 shows a kit including a plurality of spinal stabilizing rods, in accordance with certain preferred embodiment of the present invention.

Referring to FIG. 6, in certain preferred embodiments of the present invention, a kit 50 may include a plurality of stabilizing rods 52A, 52B having different lengths. The stabilizing rods 52 are preferably used for stabilizing different sections of a spinal segment. The stabilizing rods 52 desirably have a curvature that generally matches the curvature normally found in a particular spinal segment. Thus, stabilizing rods having different lengths and/or curvatures may be provided. The kit 50 preferably includes a holder 54 having a plurality of openings 56 for holding the spinal rods 52.

Figure 7:
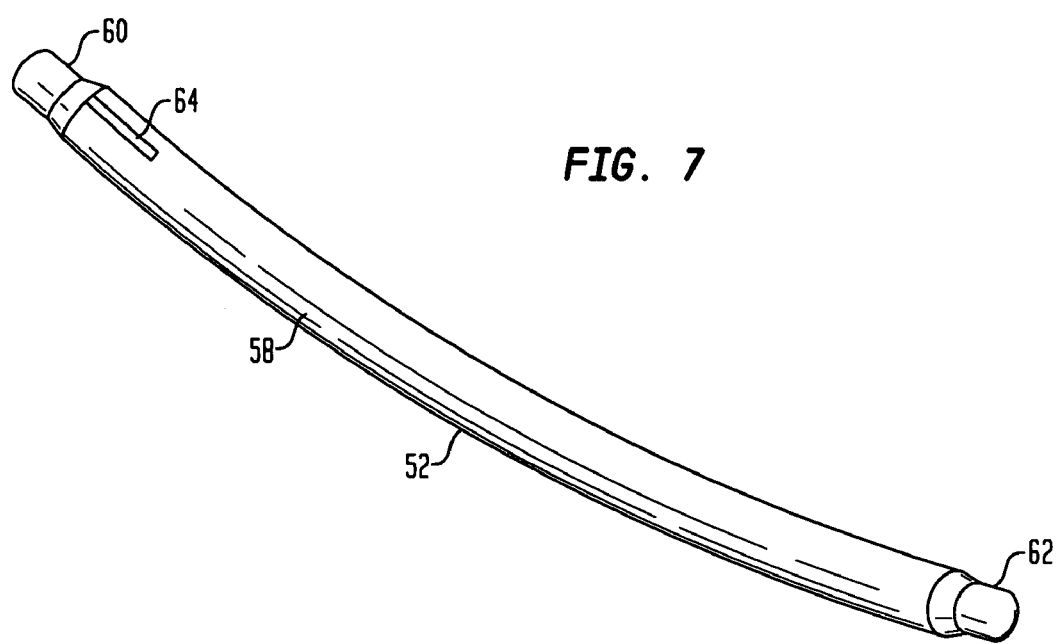
FIG. 7 shows one of the spinal stabilizing rods shown in FIG. 6.

Referring to FIG. 7, in one preferred embodiment of the present invention, a spinal stabilizing rod 52 has an elongated shaft 58 that extends between a first end 60 and a second end 62. The elongated shaft 58 preferably has an outer surface that may have a generally cylindrical shape. As shown in FIG. 7, the first and second ends 60, 62 of the elongated shaft 58 have reduced diameter sections. The collapsible ball socket 46 shown in FIG. 3 preferably fits over the reduced diameter ends 60, 62 of the spinal rod 52. The reduced diameter or tapered ends 60, 62 preferably allow for easy attachment of the ball socket 46 over the ends of the stabilizing rod.

As shown in FIG. 7, the reduced diameter ends 60, 62 have curved surfaces. In certain preferred embodiments, the reduced diameter ends have a spherical shape. The spherical shape and/or reduced diameter ends desirably enable easier movement of the rods through the tissue during a surgical procedure. In addition, the reduced diameter ends 60, 62 enable the distal end 24 of the insertion tool 20 (FIG. 1A) to be made smaller.

Although the particular embodiment shown in FIGS. 6 and 7 show stabilizing rods having reduced diameter ends, in other preferred embodiments of the present invention, it is contemplated that conventional stabilizing rods having a constant diameter along the length thereof may be used in conjunction with the tools shown and described herein.

In certain preferred embodiments, one or more stabilizing rods 52 may include an alignment marking 64 that may be used by a surgeon for orienting the stabilizing rod. As is evident in FIGS. 6 and 7, some stabilizing rods may have a curvature. The alignment markings 64 may be used by a surgeon to properly orient the rod so that the surgeon may identify the axis upon which the stabilizing rod curves. In the particular embodiment shown in FIG. 7, the alignment marking 64 is provided at the first end 60 of the stabilizing rod 52. In other preferred embodiments, however, the alignment marking 64 may extend along the length of the stabilizing rod, may be provided at both the first and second ends of the stabilizing rod, or may be provided intermittently along the length of the stabilizing rod. In still other preferred embodiments, a series of alignment markings may be provided around the outer surface of the stabilizing rod. In these particular preferred embodiments, a first marking may indicate that the opposite end of the rod is curving toward the surgeon and a second marking may indicate that the opposite end of the rod is curving away from the surgeon. The alignment marking 64 is preferably used by the surgeon for identifying the curvature of the spinal rod. In instances where the surgeon has to release an end of the spinal rod from the collapsible ball socket for repositioning the rod inserter relative to the spinal rod, the alignment marking 64 may be used after the rod has been re-secured by the clamping tip of the rod inserter.

Figure 8:
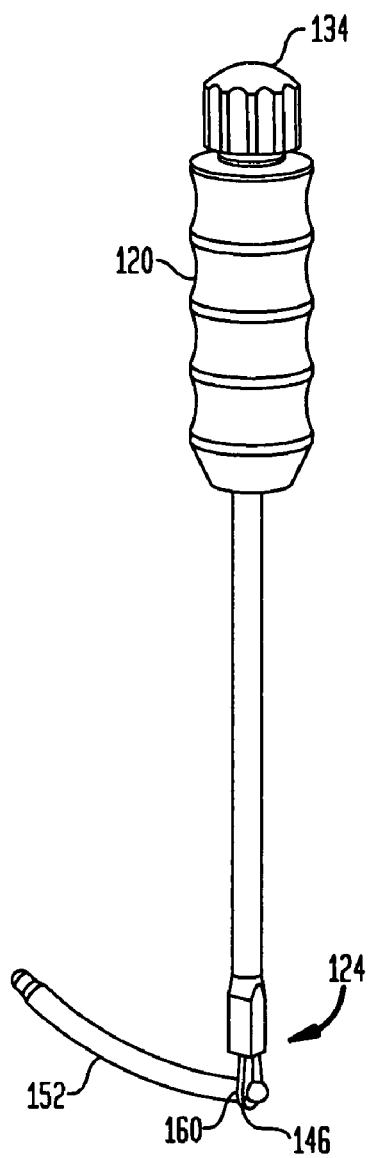
FIG. 8 shows the rod inserter tool of FIGS. 1A-1D holding an end of one of the spinal stabilizing rods shown in FIG. 6.
Figure 9:
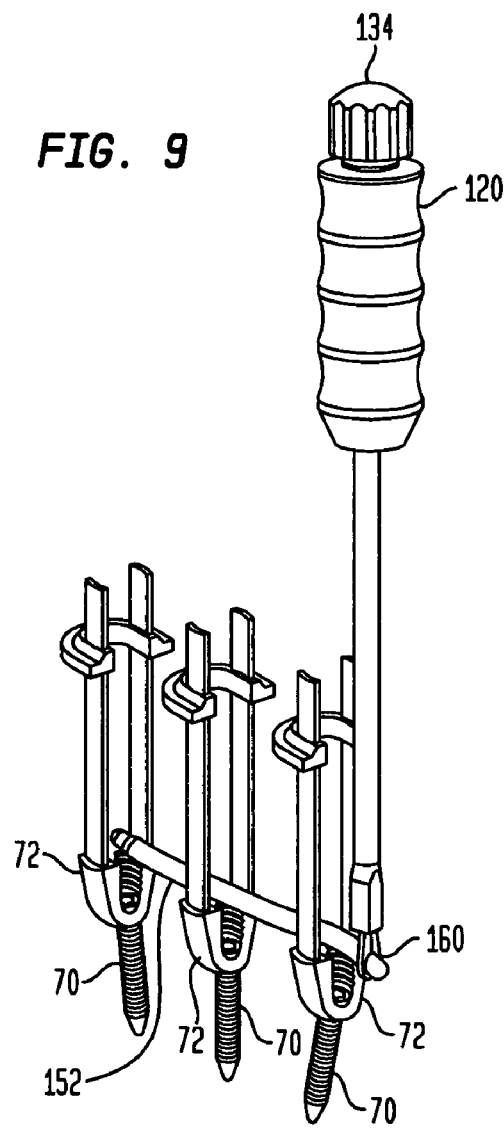
FIG. 9 shows a spine rod being seated in the heads of pedicle screws, in accordance with certain preferred embodiments of the present invention.
Figure 10:
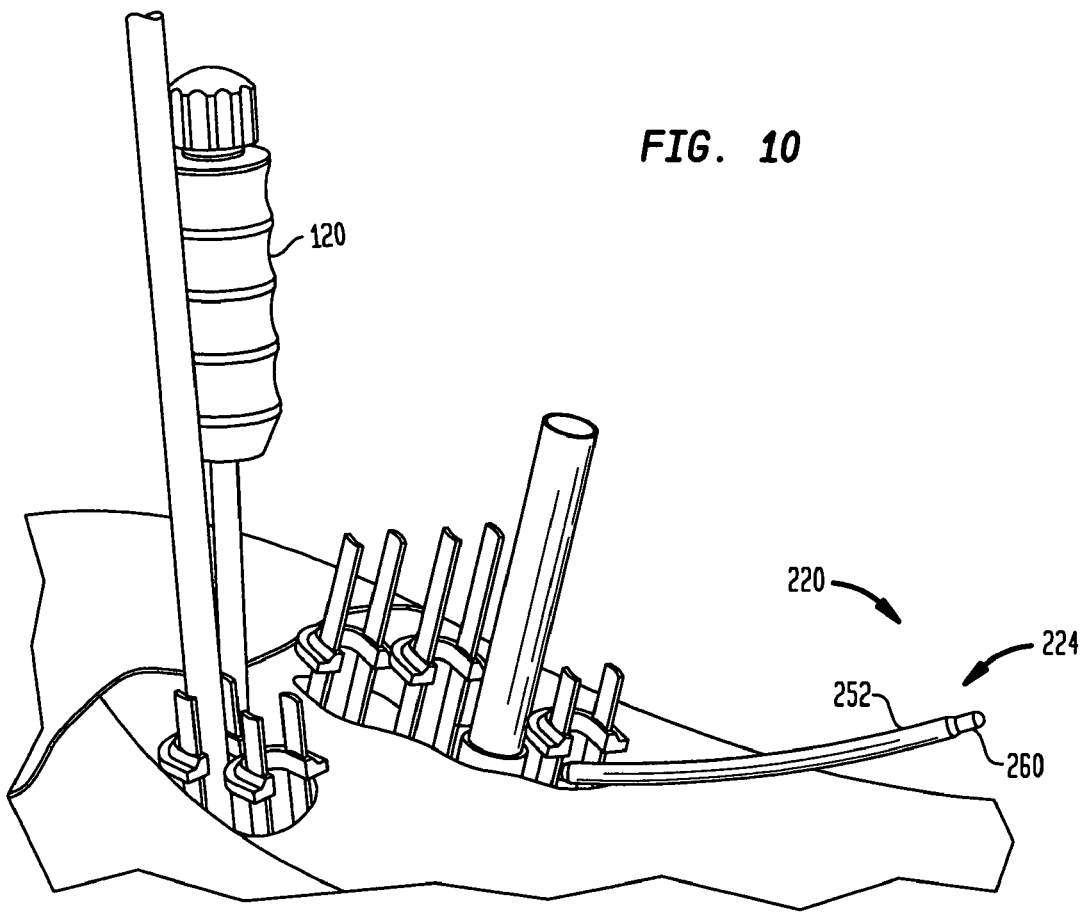
FIG. 10 shows a surgical procedure during which the spinal stabilizing rods of FIGS. 6 and 7 are coupled with the heads of pedicle screws using the rod inserter tool shown in FIGS. 1A-1D, 2A-2B and 3.

FIGS. 8-10 show the rod inserter 20 and stabilizing rods described above during spinal surgery. Referring to FIGS. 8 and 9, after pedicle screws 70 have been anchored in vertebral bone, a first rod inserter 120 is used for securing a spinal rod 152 and seating the spinal rod in the heads 72 of the pedicle screws. The ball socket 146 at the distal end 124 of the rod inserter 120 engages a reduced diameter end of the stabilizing rod 152. As shown in FIG. 8, the stabilizing rod 152 has a curvature. The alignment marking shown in FIG. 7 may be used for properly orienting the stabilizing rod as it is inserted into the heads 72 of the pedicle screws 70 shown in FIG. 9. When inserting the stabilizing rod, the surgeon may need to reposition to ball socket relative to the end of the stabilizing rod to improve the insertion technique and/or obtain better leverage for inserting the stabilizing rod. In order to reposition the clamping tip over the end 160 of the stabilizing rod 152, the rotatable knob 134 may be rotated for loosening the clamping tip relative to the end of the stabilizing rod. Once the clamping tip has been properly repositioned over the end of the stabilizing rod, the rotatable knob may be tightened for once again clamping the clamping tip and the compressible ball over the end of the rod.

During a surgical procedure, more than one rod inserter may be used. Referring to FIG. 10, a second rod inserter 220 has a distal end 224 that is secured to a reduced diameter end 260 of a second spinal stabilizing rod 252.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An inserter tool for coupling a spinal rod with an implant comprising:
    an outer shaft having a proximal end, a distal end and an elongated opening extending between the proximal and distal ends;
    a handle secured to the proximal end of said outer shaft;
    an inner shaft having a proximal end and a distal end, said inner shaft being telescopically received within the elongated opening of said outer shaft and being adapted to move between the proximal and distal ends of said outer shaft;
    a compressible clamping tip secured to the distal end of said inner shaft, said clamping tip including a first section having a proximal end and a distal end, said proximal end of said first section secured to the distal end of said inner shaft, a flexible arm that extends from the distal end of the first section, and an opening disposed between the first section and the flexible arm;
    a knob coupled with the proximal end of said inner shaft, said knob being rotatable in a first direction for extending said clamping tip from the distal end of said outer shaft and in a second direction for retracting said clamping tip into the distal end of said outer shaft so as to compress the flexible arm of said clamping tip toward the first section of said clamping tip.

2. The inserter tool as claimed in claim 1, further comprising a socket disposed in the opening of said clamping tip, said socket having a slot that enables said socket to be compressed.

3. The inserter tool as claimed in claim 2, wherein said socket is a ball socket having an aperture adapted to receive a stabilizing rod.

4. The inserter tool as claimed in claim 3, wherein the opening of said clamping tip defines an inner surface and said ball socket has an outer surface with a plurality of notches formed therein that are adapted to engage the inner surface of the opening.

5. The tool as claimed in claim 1, wherein said inner shaft extends through said handle for being attached to said knob.

6. The tool as claimed in claim 5, wherein the proximal end of said inner shaft has threads and said knob has a female opening with internal threads that are adapted to receive the threads of said inner shaft.

7. The tool as claimed in claim 1, wherein said clamping tip has a hook shape and the flexible arm of said clamping tip has a shoulder that is engageable with the distal end of said outer shaft when said inner shaft is retracted relative to said outer shaft.

8. The tool as claimed in claim 7, wherein the flexible arm of said clamping tip is connected with the first section of said clamping tip through a flexible intermediate section.

9. The tool as claimed in claim 8, wherein the flexible intermediate section has a curved surface that extends between the first section of said clamping tip and the flexible arm of said clamping tip.

10. The tool as claimed in claim 1, wherein said tool is adapted to engage a stabilizing rod being secured by said clamping tip.

11. The tool as claimed in claim 10, wherein said stabilizing rod has at least one end with a reduced diameter and said clamping tip is engageable with the reduced diameter end.

12. The tool as claimed in claim 11, wherein the reduced diameter end has a spherical surface and said clamping tip is engageable with the reduced diameter end.

13. The tool as claimed in claim 1, wherein said handle has a roughened surface.

14. An inserter tool comprising:
    an outer shaft having a proximal end, a distal end and an elongated opening extending between the proximal and distal ends;
    a handle secured to the proximal end of said outer shaft;
    an inner shaft telescopically received within the elongated opening of said outer shaft and being adapted to move between proximal and distal ends of said outer shaft;
    a clamping tip secured to a distal end of said inner shaft, said clamping tip including a first section secured to the distal end of said inner shaft, a flexible arm that extends from the first section, and an opening disposed between the first section of said clamping tip and the flexible arm of said clamping tip wherein said clamping tip has a distal end having a closed end defining at least a portion of a perimeter of said opening;
    a knob coupled with a proximal end of said inner shaft, said knob being rotatable in a first direction for extending said clamping tip from the distal end of said outer shaft and in a second direction for retracting said clamping tip into the elongated opening at the distal end of said outer shaft so as to compress the flexible arm of said clamping tip toward the first section of said clamping tip.

15. The tool as claimed in claim 14, further comprising a stabilizing rod being securable by said clamping tip.

16. The tool as claimed in claim 15, wherein said stabilizing rod has first and second ends with at least one of the first and second ends having a reduced diameter relative to a remainder of said stabilizing rod.

17. The tool as claimed in claim 16, wherein the reduced diameter end of said stabilizing rod has a spherical surface.

* * * * *